United States Patent [19]

Labarre et al.

[11] Patent Number: 4,595,682

[45] Date of Patent: Jun. 17, 1986

[54] TRICYCLOPHOSPHAZENE DERIVATIVES, AND THEIR APPLICATION AS CANCER CHEMOTHERAPEUTIC DRUGS

[75] Inventors: Jean-François Labarre, Toulouse; Guy Guerch, Castanet; Gaston Levy, Balma; François Sournies, Ramonville St Agne, all of France

[73] Assignee: Centre National de la Recherche Scientifique (CNRS), Paris, France

[21] Appl. No.: 554,812

[22] Filed: Nov. 23, 1983

[30] Foreign Application Priority Data

Nov. 25, 1982 [FR] France .................. 82 19768

[51] Int. Cl.[4] .................. C07D 203/06; A61K 31/395
[52] U.S. Cl. .................. 514/83; 260/239 EP
[58] Field of Search .................. 260/239 EP; 514/83

[56] References Cited

U.S. PATENT DOCUMENTS

| | | | |
|---|---|---|---|
| 3,197,464 | 7/1965 | Ottmann et al. | 260/239 EP |
| 3,299,128 | 1/1967 | Allcock et al. | 260/543 PN |
| 3,311,622 | 3/1967 | Joffre | 260/239 EP |
| 4,469,687 | 9/1984 | Labarre et al. | 544/337 X |

OTHER PUBLICATIONS

De Ruiter et al., Chem. Abstracts vol. 98 (1983) p. 612 Abstract #107410g.

Prakash, Chem. Abstracts vol. 95 (1981) p. 695 Abstract #25005e.

Ristich et al., J. Econ. Entom., vol. 58(5), (1965) pp. 929–932.

Derwent Abstract of NL 8007-107 (Jul.-16-82), Abstract 67375 E/32, Derwent Class B05.

Derwent Abstract of DT 2043128 (Mar.-02-72), Abstract 16886T-B, Derwent Class B3.

Krishnamwthy, et al., Chemical Abstracts, vol. 93, (1980), Entry 114613c.

Primary Examiner—Donald G. Daus
Assistant Examiner—William A. Teoli, Jr.
Attorney, Agent, or Firm—Thomas J. Greer, Jr.

[57] ABSTRACT

The present invention especially relates to compounds of the formula:

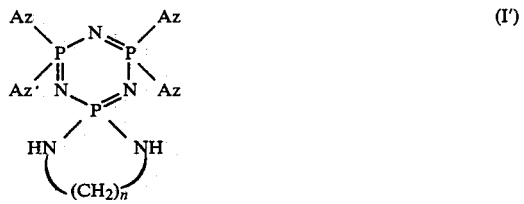

in which Az is an aziridinyl radical and n is an integer from 1 to 5, a process (sic) for their preparation, and their application as anti-cancer drugs.

9 Claims, 9 Drawing Figures

FIG_1

FIG_9

TRICYCLOPHOSPHAZENE DERIVATIVES, AND THEIR APPLICATION AS CANCER CHEMOTHERAPEUTIC DRUGS

The present invention relates to novel chemical compounds, processes for their preparation and the application to these compounds as drugs.

It was in 1979 (J-F. Labarre, J-P. Faucher, G. Levy, F. Sournies, S. Cros and G. Francois, Europ. J. Cancer, 15, (1979), 637) that the anti-tumoral activity in vivo on P388 and L1210 leukemias and on subcutaneous B16 melanoma (grafted onto female DBA/2 mice) of hexaziridinocyclotriphosphazene $N_3P_3Az_6$ was numerically substantiated for the first time.

The EORTC Laboratories subsequently provided proof that this activity was also exerted to a significant degree on 18 other tumors, amongst which there may be mentioned line 26 carcinoma of the colon, Lewis carcinoma of the lung, P815 mastocytoma, line 16 breast carcinoma, ependymoblastoma and Yoshida sarcoma.

This very broad spectrum of activity on tumors in the mouse, coupled with the low mutagenicity of the molecule in question (EORTC code name: MYKO 63) made it a drug whose development with a view to use in human clinical treatment could reasonably be envisaged.

However, it proved very rapidly that MYKO 63 in reality suffered from the appearance of a troublesome cumulative toxicity in the course of type 5 Q3D or 5 Q4D polyinjection protocols. MYKO 63 was thus an anti-tumoral substance which was too slow in respect of the kinetics of its action on the tumor, and in respect of its rate of excretion.

In order to overcome the disadvantages associated with the use of MYKO 63, derivatives having related structures have been developed, namely the cyclodiphosphathiazenes $(NpAz_2)_2NSOX$ (X=F:SOF; X=Ph:SOphi; X=Az:SOAz).

SOF, SOphi and especially SOAz exhibit a noteworthy activity, substantially equal, in monoinjection usage, to that of MYKO 63, but with all cumulative toxicity having disappeared, even in heavy Q3D and Q4D protocols.

SOAz is currently in phase 2 human clinical usage.

In spite of the success thus recorded, especially with SOAz, as regards the improvement of the pharmacokinetics of MYKO 63 by replacing a phosphorus atom in its ring by a sulfur atom, the fact still remains that the doses required for SOAz to exert a therapeutic activity are high (in the allopathy range) and that a not insignificant proportion (40%) of the amount injected is found intact in the urine of patients over the course of the 12 hours following injection. This provides evidence that the injected SOAz does not all reach the tumor and that an excessively large proportion of the drug thus does not perform its function.

The present invention accordingly relates to novel compounds having improved capability of penetration into the malignant cell, so as to increase the amount of active compound reaching the tumor.

These novel compounds have the formula I:

in which:

Az is a substituted or unsubstituted 1-aziridinyl radical,

A is a straight or branched, substituted or unsubstituted, alkylene, alkenylene or alkynylene chain, which can be interrupted by one or more divalent radicals —$NR_3$—, —S— or —O—, and $R_1$, $R_2$ and $R_3$ can, independently of one another, be:
a hydrogen atom,
a substituted or unsubstituted alkyl radical,
a substituted or unsubstituted alkenyl radical,
a substituted or unsubstituted alkynyl radical or
a substituted or unsubstituted aryl radical.

Though in the compounds of the formula I the radical Az is preferably an unsubstituted 1-aziridinyl radical, the 1-aziridinyl radical can be substituted by 1 to 4 $C_1$–$C_3$ alkyl or alkoxy radicals.

The —A— chain can contain from 1 to 5 carbon atoms. —A— is preferably an alkylene chain. It can be an uninterrupted carbon chain or be interrupted by one or more —$NR_3$—, —O— or —S— radicals, preferably by 1 to 4 radicals oof this type.

Preferably, the radicals $R_1$, $R_2$ and $R_3$ are:
a hydrogen atom or
an unsubstituted or substituted alkyl radical.

These radicals $R_1$, $R_2$ and $R_3$ can moreover be substituted, like the —A— chain, by one or more halogen atoms, imino radicals, amino radicals or aryl radicals which are unsubstituted or substituted by one or more halogen atoms or $C_1$–$C_3$ alkyl radicals.

By "alkyl radical" there are more especially to be understood straight or branched lower alkyl radicals, in particular having from 1 to 7 carbon atoms, such as the methyl, ethyl, n-propyl and isobutyl radicals.

By "alkenyl radical" there are more especially to be understood straight or branched lower alkenyl radicals, in particular having from 2 to 7 carbon atoms and containing one or more ethylenic unsaturated bonds, for example the ethylenyl radical.

By "alkynyl radical" there are more especially to be understood straight or branched lower alkynyl radicals, in particular having 2 to 7 carbon atoms, such as the acetylenyl or propargyl radicals.

By "aryl radical" there are essentially to be understood monocyclic radicals, in particular the phenyl radical; the aryl radical may be substituted in various way, in particular by alkyl radicals, as for example in the tolyl or xylyl radicals.

Amongst the substituents on carbon atoms of the —A— chain, the imino or amino radicals deserve special mention.

As substituents $R_3$, the alkylamino radicals deserve special mention.

The present invention in particular relates to the compounds of the formula I':

(I')

where n is an integer from 1 to 5 and preferably is chosen from amongst 2, 3, 4 and 5.

If n is 3, the compound has the formula:

This product will be referred to as SPIRODIAM 3.

If n is 4, the compound has the formula:

This product will be referred to as SPIRODIAM 4.

The present invention also relates to the processes of preparation of the compounds of the formula I, in which:

(a) the polyamine of the formula II:

$H(R_1N)-A-(NR_2)H$ (II)

is reacted with the geminal dichlorinated compound of the formula III:

(III)

(b) an excess of the substituted or unsubstituted aziridine is reacted with the compound of the formula IV:

(IV)

The compound of the formula III is sometimes referred to as MYCLAz.

The compounds of the formulae III and IV can be prepared from the hexachloro derivative $N_3P_3Cl_6$, either by reacting it with the aziridine to prepare the compound of the formula III, or by reacting it with the polyamine $H(R_1N)-A-(NR_2)H$ to give the compound of the formula IV.

These various reactions are preferably carried out in the presence of a binder for HCl, which is preferably an amine which does not react with the basic ring, such as a tertiary amine, for example a trialkylamine, or in the presence of the reagent in an excess over what is required for the reaction which it is desired to favor.

Thus, in the second stage of the process, for converting III or IV to I, a large excess of the reagent may be used, greater than corresponds to a ratio of 2:1 if required for III, or than corresponds to 4:1 if required for IV; on the other hand, in the presence of an acid acceptor, it is possible to use a ratio of 1:1 in the case of III and of 2:1 in the case of IV.

These reactions are preferably carried out in a solvent such as an ether or a halogenated solvent or a mixture of such solvents, for example a mixture of 60°-80° petroleum ether and methylene chloride in the ratio of 4:1, and preferably takes place at a temperature of between $-20°$ and $+20°$ C., for example at about 0° C., and in an inert atmosphere (namely under carefully dried $N_2$ or Ar).

Amongst the polyamines which may be used in the preparation of the compounds according to the invention, there may be mentioned propylenediamine, putrescine and cadaverine, which lead to compounds I'.

Lastly, the reaction product of tthe formula I may be purified by known methods, for example solvent extraction, crystallization, liquid phase chromatography and high performance liquid phase chromatography ("HPLC").

The various starting products which may be used in carrying out the processes according to the present invention may in particular be prepared by the methods described in the following publications:

Y. Kobayashi, L. A. Chasin, and L. B. Clapp, Inorg. Chem. 2 212 (1963),

R. Ratz, E. Kober, C. Grundmann and G. Ottmann, Inorg. Chem., 3, 757 (1964) and U.S. Pat. No. 3,197,464 of 27th July 1965, G. Guerch, J-F. Labarre, F. Sournies, M. Manfait, F. Spreafico and S. Filippeschi, Inorg. Chim. Acta 66, 175-183 (1982), in the case of gem-$N_3P_3Az_4Cl_2$, and M. Becke-Goehring and B. Boppel, Z. Anorg. Allg. Chem., 322, 239 (1963), S. S. Krishnamurthy, K. Ramachandran, A. R. Vasudeva Murthy, R. A. Shaw and M. Woods, Inorg. Nucl. Chem. Lett., 13, 407 (1977), G. Guerch, M. Graffeuil, J-F. Labarre, R. Enjalbert, R. Lahana and F. Sournies, J. Mol. Struct., 85, 000 (1982), G. Guerch, J-F. Labarre, R. Roques, and F. Sournies, J. Mol. Struct., 85, 000 (1982)

in the case of the spiro-$N_3P_3Cl_4$ [$POLYAM_{m,n}$] compounds.

Finally, the present invention provides, as novel drugs, certain compounds described above as well as pharmaceutical compositions which contain, as the active principle, at least one of these compounds, and in particular pharmaceutical compositions for parenteral administration.

Amongst the compositions for parenteral administation there may be mentioned compositions for injection, especially intraperitoneal and intravenous injection, though other compositions, such as pellets, may be used. Since the products in question are generally rather soluble in water, the pharmaceutical vehicle used is preferably an aqueous solvent, for example a physiological sodium chloride solution. Of course, in the case of products which are difficult to solubilize, there may be used a buffer which keeps the pH constant or, where appropriate, a nonaqueous solvent such as one of the esters, alcohols, polyols or various oils, in combination with emulsifiers. It is also possible to use suspensions, in particular suspensions in hydroxypropylcellulose solutions.

Though the pharmaceutical compositions according to the present invention are preferably injectable compositions, there may also be used compositions for digestive, sublingual, oral or rectal administration; these compositions may be provided in a solid form, for example as tablets, cachets, pellets, capsules or suppositories, or as a liquid, for example as drops or in ampoules.

The compositions for oral administration are formulated with known solid carriers, for example gelatine, gum arabic, lactose, starch, polyalkylene glycol or carboxymethylcellulose.

In the case of suppositories, polyethylene glycol or lanoline may be used as the vehicle.

The compositions according to the present invention can also be administered topically, especially as an ointment or gel, containing an inert vehicle such as vaseline, polyethylene glycol or other fatty excipients, and suitable for application to the skin; an agent which facilitates penetration of the active principle through the skin may also be present.

In general, the compositions according to the present invention can contain various adjuvants such as preservatives, stabilizers, wetting agents, emulsifiers, texturing agents, disintegrating agents, flavorings and colorants.

The compounds according to the present invention have proved especially active in the treatment of certain tumors. They have in particular proved very active against two standard tumors, namely P388 leukemia and P815 mastocytoma.

These compounds can essentially be used by injection, especially by intraperitoneal or intravenous injection. Since these compounds are highly water-soluble, the preparation of injectable compositions presents no problem whatsoever. The doses administered of course depend in each case on the type of tumor to be treated as well as on the general condition of the patient and can vary very widely, in particular between 1 mg/kg/day and 100 mg/kg/day, these doses being given as a single injection or several injections, in which latter case the frequency may be varied.

The examples which follow illustrate the preparation and activity of some of the compounds of the present invention, without thereby implying any limitation of the invention.

EXAMPLE 1

Preparation of the compound spiro-$N_3P_3Az_4$[NH—$(CH_2)_3$—NH] via synthesis of the compound gem-$N_3P_3Az_4Cl_2$ A solution of 87.0 millimoles of freshly distilled propylenediamine [$H_2N$—$(CH_2)$—$_3$—$NH_2$] in 50 ml of a 4:1 mixture of 60°–80° C. petroleum ether and $CH_2Cl_2$ (this mixture hereafter being referred to as S) is added dropwise, over 2 hours, to a solution of 32.0 millimoles of gem-$N_3P_3Az_4Cl_2$ in 150 ml of the same solvent S, at ambient temperature and with vigorous stirring. Magnetic stirring is continued overnight. The propylenediamine hydrochloride formed is filtered off and the solvent of the mother solution is evaporated in vacuo. The crude reaction product gives two spots in thin layer chromatography (with methanol as the eluant), at Rf=0.17 and 0.68.

Recrystallization of this crude product from 20 volumes of anhydrous $CCl_4$, partially evaporating the solvent and subsequently cooling the solution, gives a crystalline compound (Rf=0.68) having a melting point of 134° C., the yield being 80%.

The compound exhibits the following analytical characteristics:

Analysis: Calculated: C 35.20, H 6.44, N 33.59, P 24.76, Found: C 34.98, H 6.40, N 33.38, P 24.59, C 35.10, H 6.50, N 33.70, P 24.83.

Mass spectrum: m/z 375 (M)+ 38.2%, 333 (M-1Az)+ 100%, 292 (M-2Az)+ 29.2%, 249 (M-3Az)+ 17.9%, 208 (M-4Az)+ 12.9%, 304 ($N_3P_3Az_4$)+ 9.5%, 261 ($N_3P_3Az_3$)+ 10.6%, 220 ($N_3P_3Az_2$)+ 5.0%, 177 ($N_3P_3Az$)+ 3.3%, 135 ($N_3P_3$)+ 1.1%.

$^{31}P$ NMR in solution in $CH_2Cl_2$ (relative to 85% strength $H_3PO_4$): $AX_2$ spectrum comprising a doublet at 38.34 and 37.45 ppm and a triplet at 19.69, 18.80 and 17.91 ppm, the intensities being in the ratio 2:1. J(P-P)=32.36 Hz.

IR ($cm^{-1}$) (KBr): 3360 w, 3255 m, 3050 w, 2985 m, 2958 w, 2925 vw, 2880 w, 2860 w, 1255 s, 1180 vs, 1160 m, 1150 m, 1080 s, 930 vs, 870 m, 840 m, 800 m, 703 s, 640 s, 510 s, 497 sh, 440 m.

Figure 1:
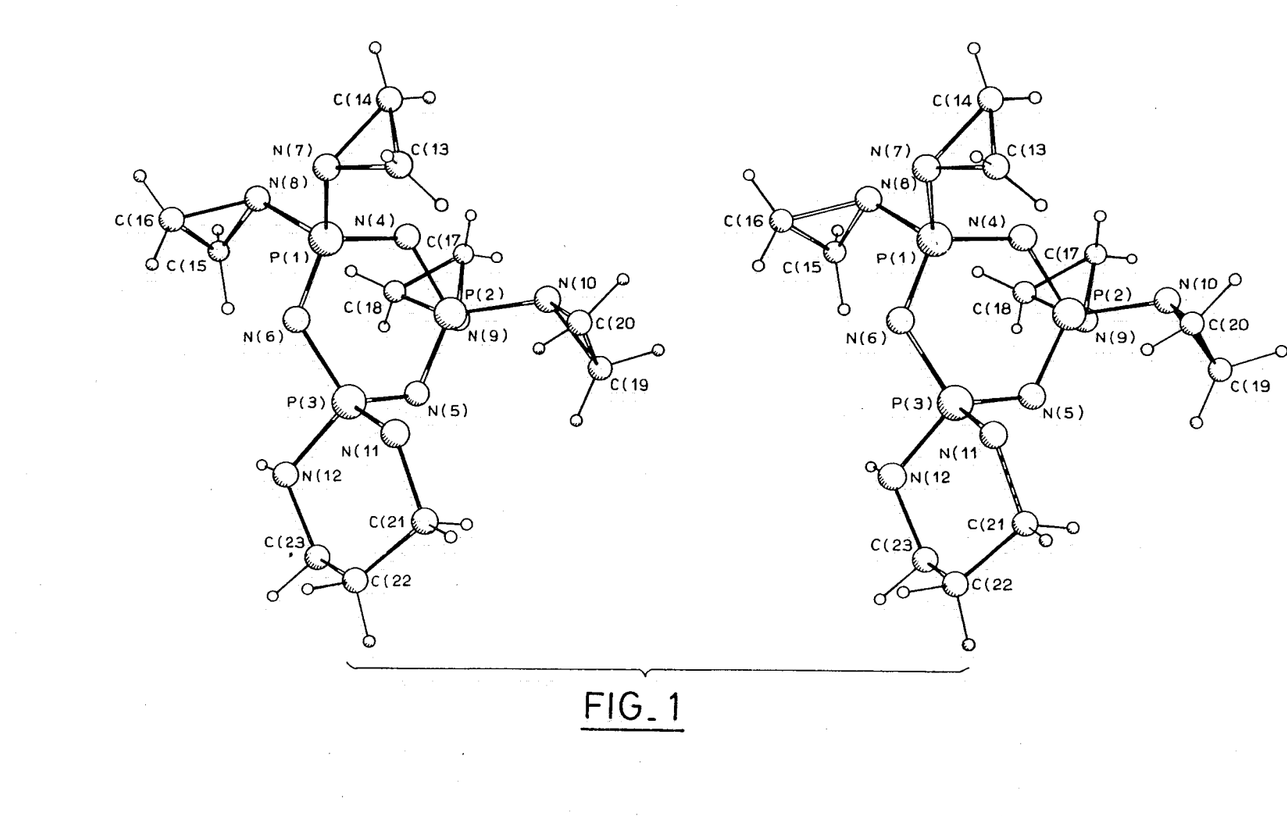

Structure by X-ray analysis: Space group $P2_1/a$, a=18.369(3)Å, b=9.715(1)Å, c=9.722(2)Å, α=90°, β=94.79(1)°, γ=90°, V=1728.9(5)Å$^3$, Z=4 (see FIGS. 1 and 2), R=0.047.

This structure demonstrates the non-planarity of the spiro loop, whilst the $N_3P_3$ ring is strictly planar within the limits of experimental error.

Figures 2, 3:
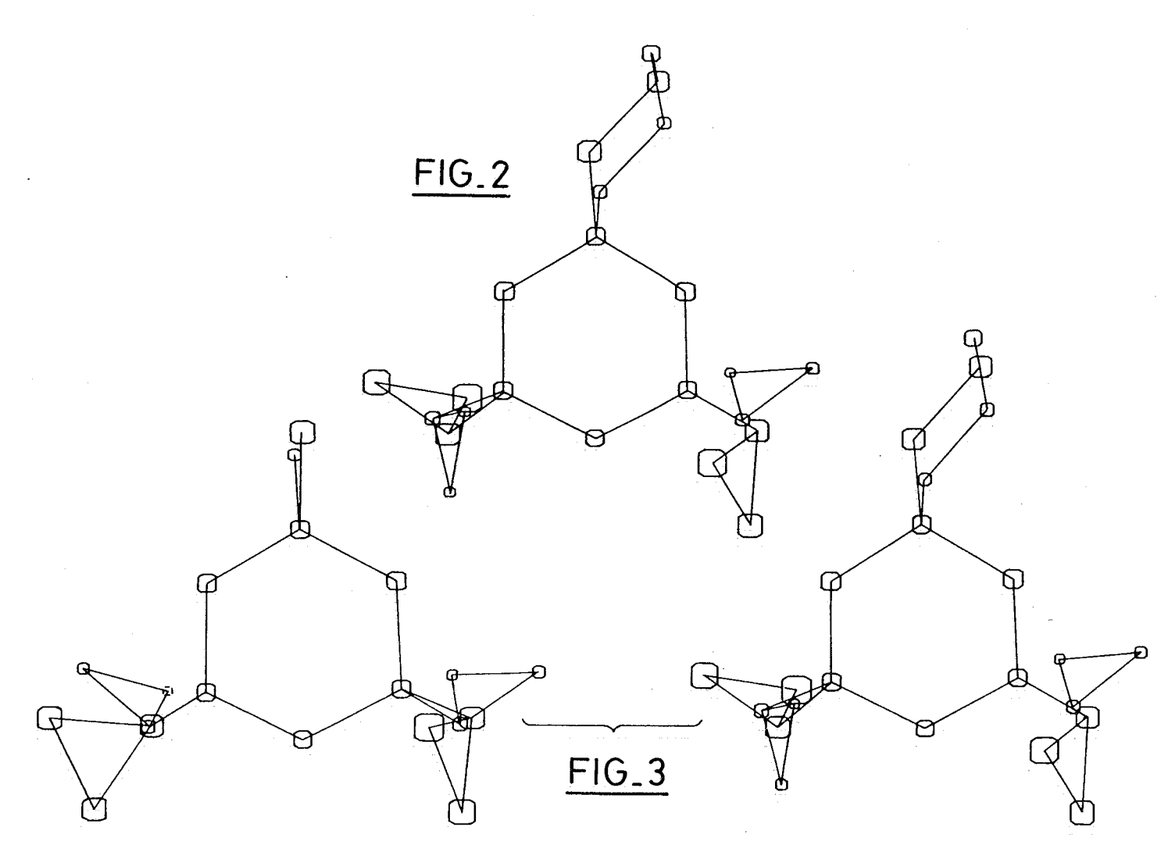
Figure 4:
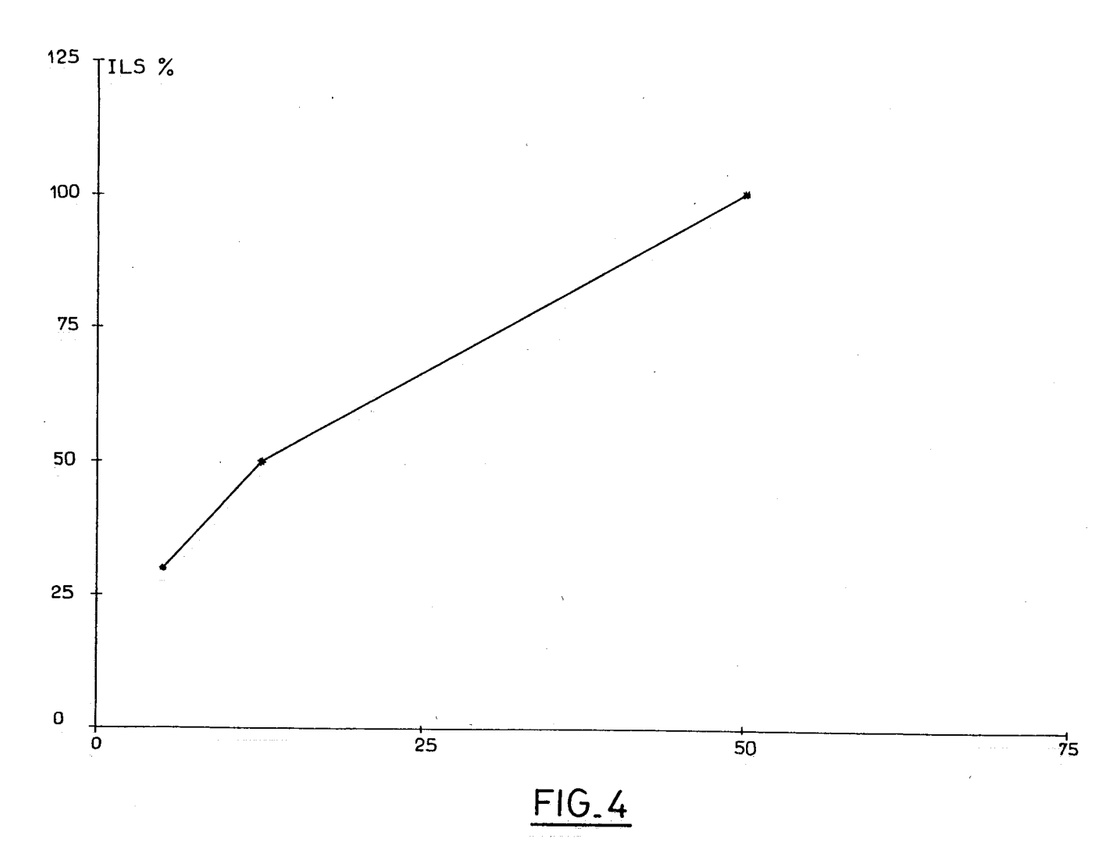
Figure 5:
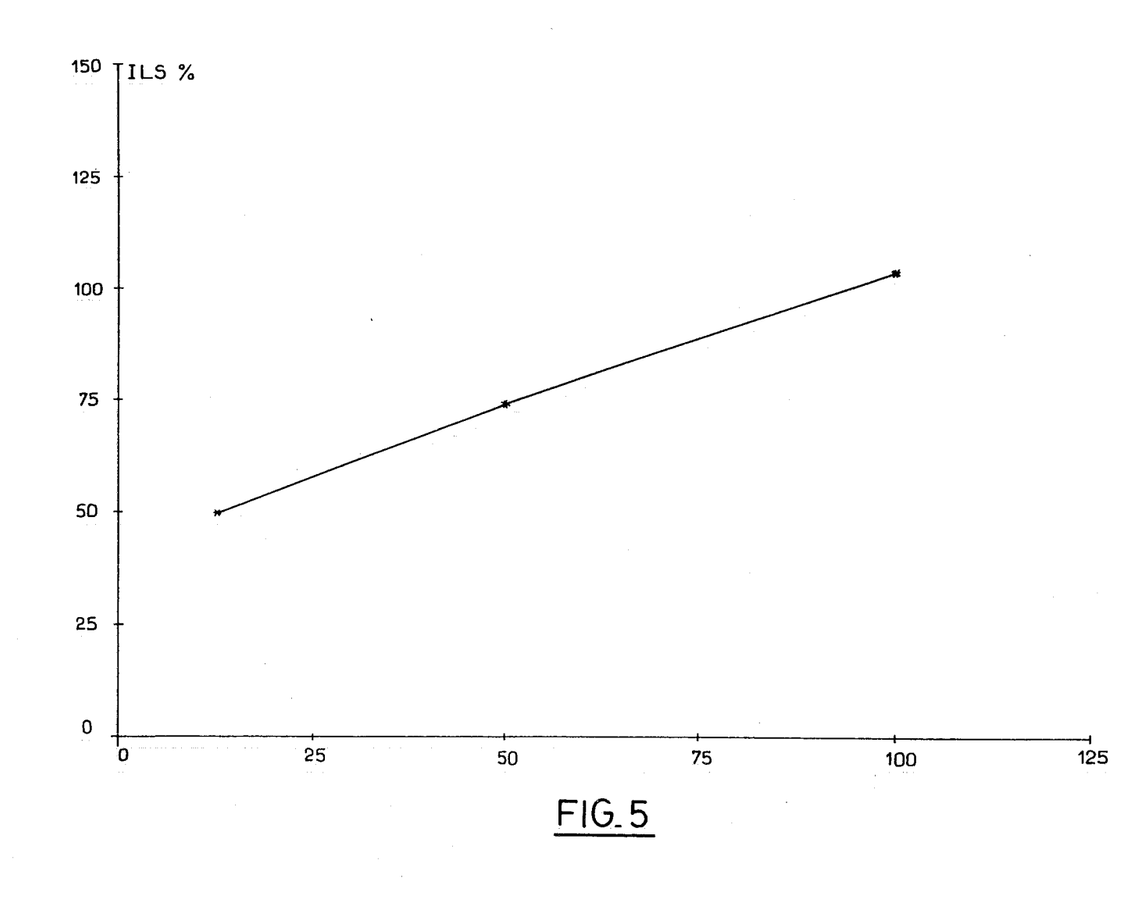
Figure 6:
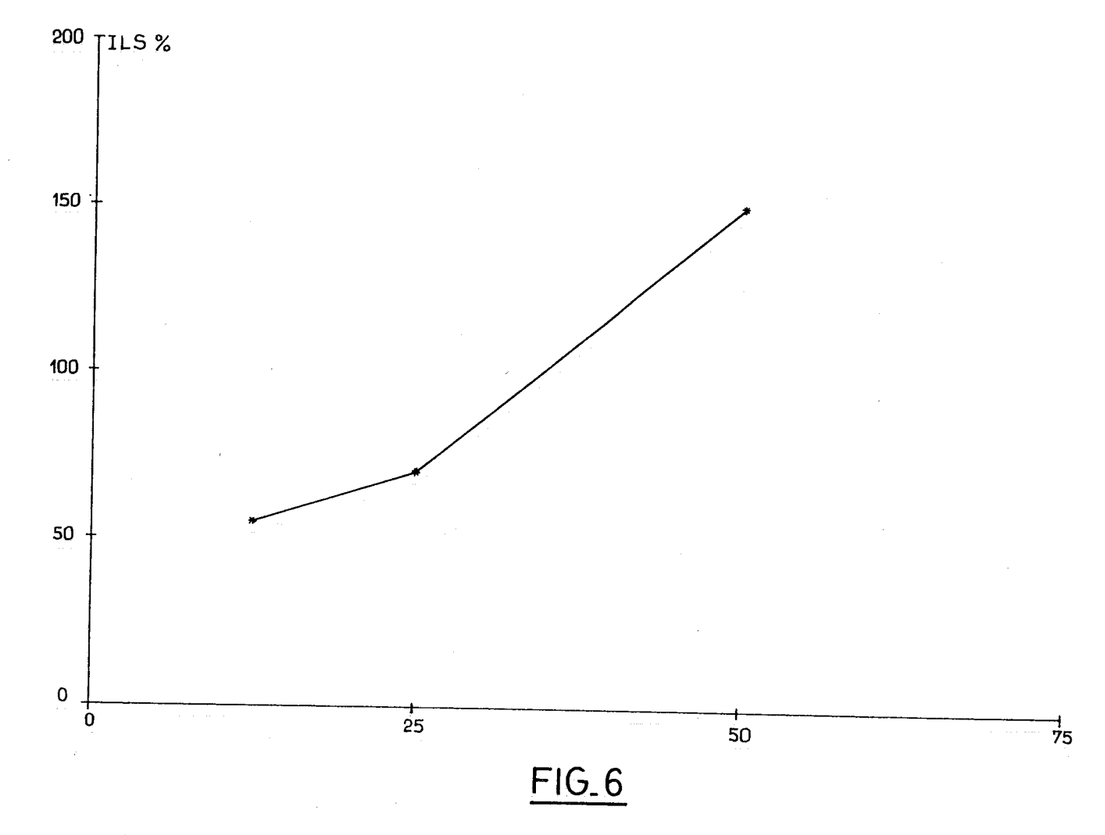
Figure 7:
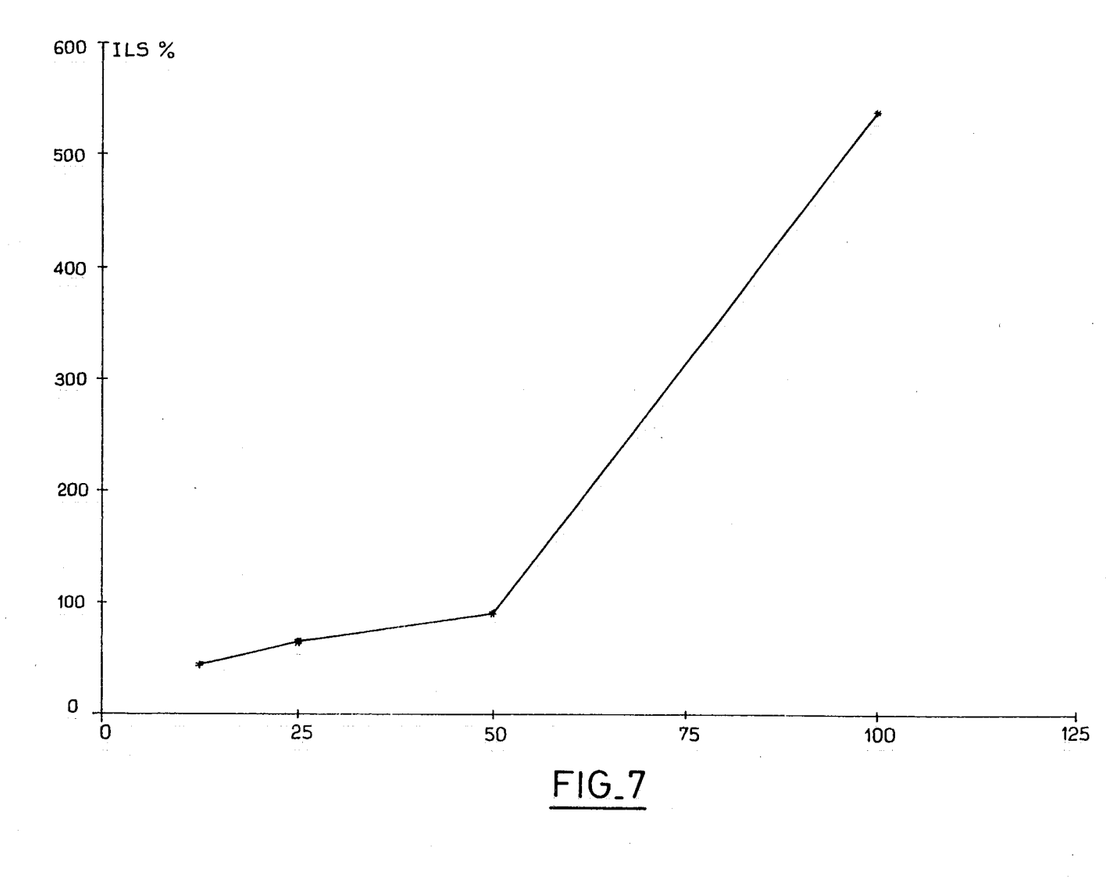
Figure 8:
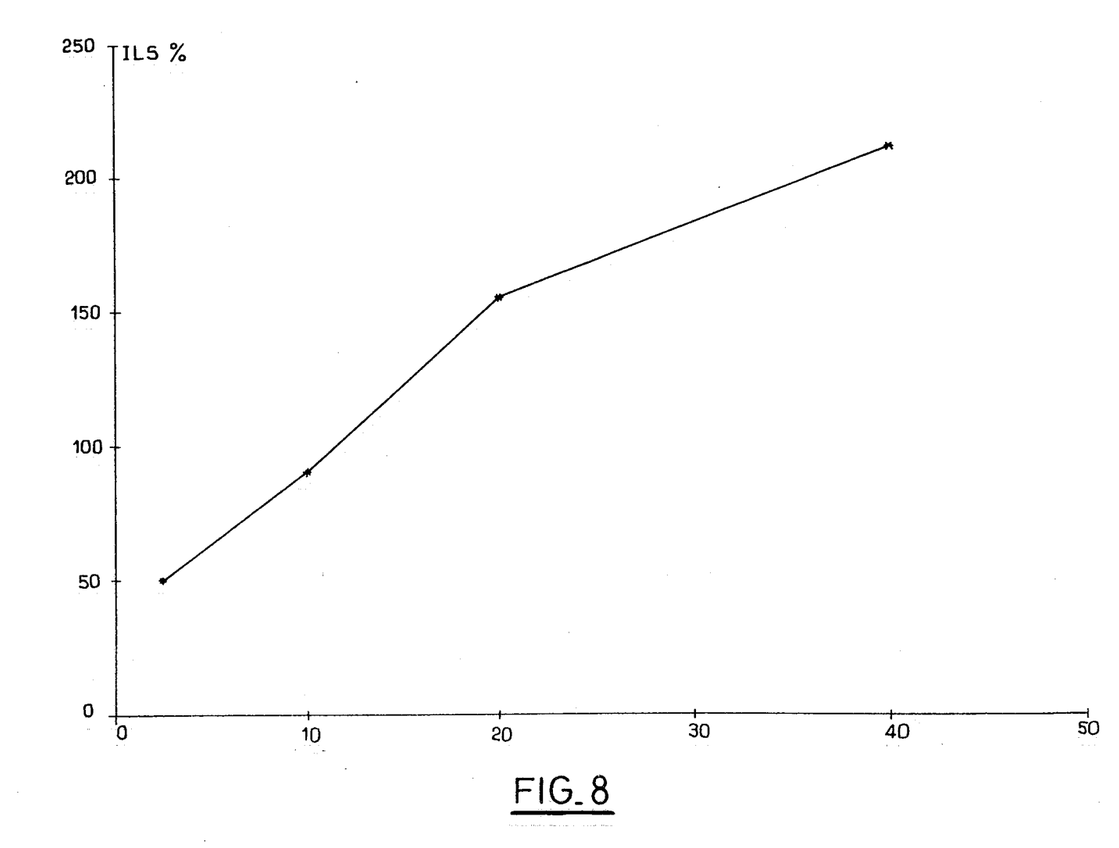
Figure 9:
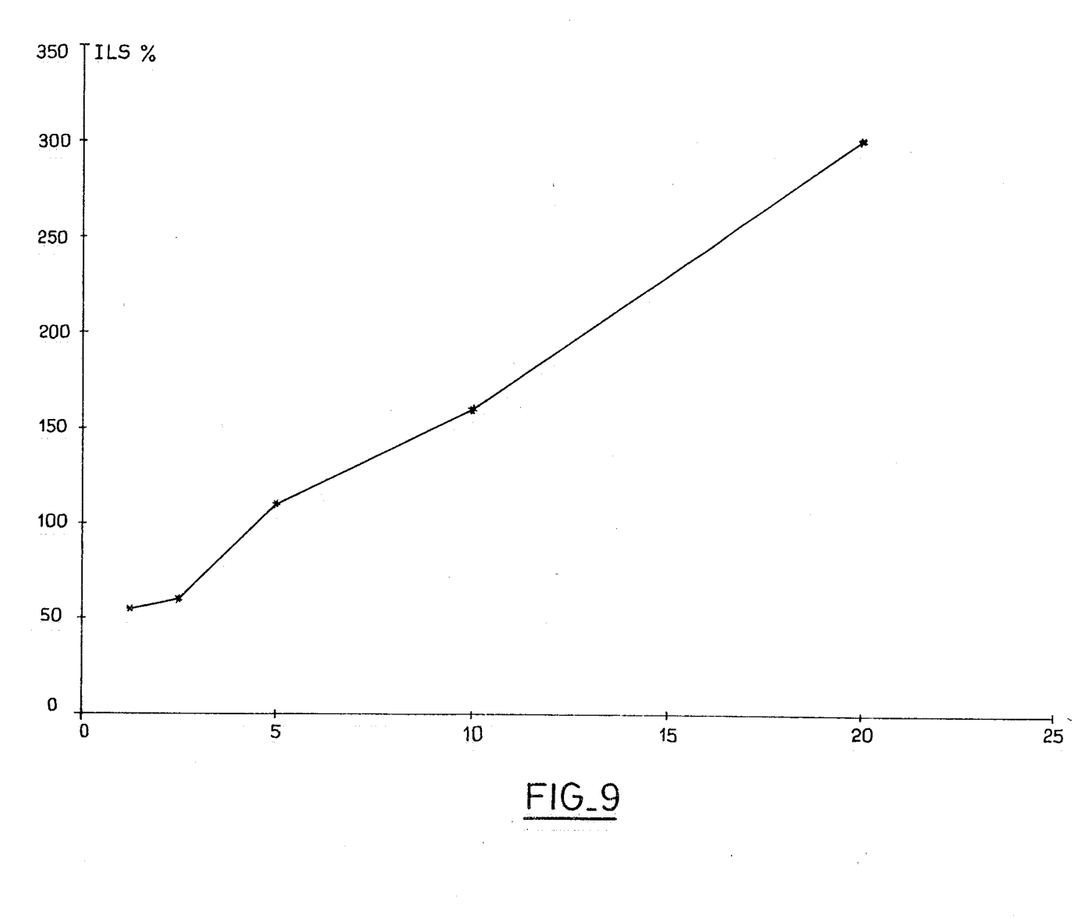

FIG. 3 moreover shows the conformational changes of the 4 aziridinyl "blades" brought about by grafting the —[HN—$(CH_2)_3$—NH]— loop onto the phosphorus, bearing 2Cl, of the compound $N_3P_3Az_4Cl_2$.

EXAMPLE 2

Preparation of the compound spiro-$N_3P_3Az_4$[HN—$(CH_2)_3$—NH] via the synthesis of the compound spiro-$N_3P_3Cl_4$[HN—$(CH_2)_3$—NH]

A solution of 48.5 millimoles of freshly distilled aziridine in 35 ml of solvent S is added dropwise over 2 hours to a solution of 11.0 millimoles of spiro- N₃P₃Cl₄[HN—(CH₂)₃—NH] and 44.5 millimoles of Et₃N in 120 ml of solvent S. The reaction is carried out at 0° C., with vigorous stirring and under an inert atmosphere (dry N₂ or Ar). The reaction mixture is allowed to return to ambient temperature and is then stirred for a further 24 hours at this same temperature.

The triethylamine hydrochloride is then filtered and the solvent of the mother solution is evaporated in vacuo. The crude reaction product at this stage still gives 2 spots in thin layer chromatography, with Rf=0.17 and 0.68.

Recrystallization from 20 volumes of CCl₄ by partial evaporation of the solvent and cooling of the solution gives the expected crystalline derivative. Melting point: 134° C., yield 87%.

This compound exhibits analytical characteristics identical to those described above for the sample obtained by the first method.

EXAMPLES 3 AND 4

Preparation of the compound spiro-N₃P₃Az₄[HN—(CH₂)₄—NH]

This compound can be synthesized by following one or other of the two working methods described above in Examples 1 and 2 for spiro- . . . (sic)[HN—(CH₂)₃—NH] and replacing propylenediamine by putrecine in the process of Example 1, and spiro-N₃P₃Cl₄—[NH—(CH₂)₃—NH] by spiro-N₃P₃Cl₄[NH—(CH₂)₄—NH] in the process of Example 2.

Regardless of the method used, the yield of pure product is 90% or more.

The analytical characteristics of this compound are as follows:

Thin layer chromatography: Rf=0.41, with CH₃OH as the eluant.

Analysis: Calculated: C 37.02, H 6.73, N 32.38, P 23.87, Found: C 36.93, H 6.70, N 32.08, P23.75, C 37.10, H 6.75, N 32.47, P 23.78.

Melting point (uncorrected): 171° C.

Mass spectrum: m/z 389 (M)+ 83.3%, 347 (M-1Az)+ 96.8%, 304 (M-2Az)+ 100%, 263 (M-3Az)+ 30.9%, 220 (M-4Az)+ 20.6%, 261 (N₃P₃Az₃)+ 36.5%, 177 (N₃P₃Az)+ 17.4%, 135 (N₃P₃)+ 3.9%.

It may be noted that the peaks at m/z 304 and 220 can also be attributed to the fragments (N₃P₃Az₄)+ and (N₃P₃Az₂)+ because the masses of 2Az and the fragment [HN—(CH₂)₄—NH] are identical, both being 84.

$^{31}$P NMR in solution in CH₂Cl₂ (relative to 85% strength H₃PO₄): AX₂ spectrum comprising a doublet at 38.74 and 37.77 ppm and a triplet at 23.65, 22.68 and 21.71 ppm, the intensities being in the ratio of 2:1. J(P-P)=35.29 Hz.

IR (cm$^{-1}$) (KBr): 3270 m, 3060 w, 2990 m, 2920 m, 2880 vw, 2865 vw, 1260 s, 1230 s, 1190 vs, 1170 s, 1120 s, 1080 w, 1055 m, 955 m, 925 vs, 855 m, 845 m, 810 m, 720 w, 705 m, 690 m, 640 s, 525 w, 435 w.

The starting compounds employed in the preceding examples can be prepared as described in the following documents, or by analogous processes: gem-N₃P₃Az₄Cl₂:

Y. Kobayashi, L. A. Chasin, and L. B. Clapp, Inorg. Chem., 2, 212 (1963),

R. Ratz, E. Kober, C. Grundmann and G. Ottmann, Inorg. Chem., 3, 757 (1964) and U.S. Pat. No. 3,197,464 of 27th July 1965

G. Guerch, J-F. Labarre, F. Sournies, M. Manfait, F. Spreafico and S. Filippeschi, Inorg. Chim. Acta, 66, 175–183 (1982);

spiro-N₃P₃Cl₄[HN—(CH₂)₃—NH]

G. Guerch, M. Graffeuil, R. Enjalbert, R. Lahana, J-F. Labarre and F. Sournies, J. Mol. Struct., 85, 000 (1982);

spiro-N₃P₃Cl₄[HN—(CH₂)₄—NH]

G. Guerch, J-F. Labarre, R. Roques and F. Sournies, J. Mol. Struct., 85, 000 (1982).

Pharmacological properties

The compounds mentioned above were tested in respect of their pharmacological activity.

It was found first of all that the solubility of the two compounds, of Examples 1 and 4, is equal to or greater than 20 g/l, which is thus amply sufficient for the preparation of injectable forms in aqueous solution.

The toxicity of these compounds was determined on Swiss or CD2F1 female mice.

The mortality which regularly manifested itself on days 5 and 6 after administration was recorded as a function of the dose inoculated and made it possible to deduce the LD₀, which corresponds to the maximum non-lethal dose. The results do not depend on the species of mouse used. It was found that:

the LD₀ of the compund spiro-N₃P₃Az₄[HN—(CH₂)₃—NH] (hereinafter referred to as SPIRODIAM 3) is 75 mg/kg, and the LD₀ of the compound spiro-N₃P₃Az₄[NH—(CH₂)₄—NH] (hereafter referred to as SPIRODIAM 4) is 125 mg/kg.

Anti-tumor activity

The anti-tumor activity tests were carried out by the Screening and Pharmacology Group of the EORTC, located at the Institute Mario Negri in Milan.

These tests were carried out either by a single injection at various doses on days J+1 following the grafting of the tumor, or by chronic Q1D polyinjections, using CD2F1 female mice.

The results observed are summarized in Table 1 below.

In this table:

$$ILS\ \% = \frac{T - C}{C} \times 100$$

where T (in days) is the mean life span of the treated mice and C (in days) is the mean life span of the comparison mice. QnD means one injection every n days starting from day J+1, and thus "5 injections Q1D" means 1 injection daily from J+1 to J+5.

The essential comments made on Table 1 are the following:

1. SPIRODIAM 3 and SPIRODIAM 4 used as Q1D polyinjections, cure both P388 leukemia and P815 mastocytoma. Cure is also achieved by monoinjection (100 mg/kg, representing 4/5 of the LD₀) with SPIRODIAM 4 in the case of P815.

2. In view of the LD₀ values indicated above, it appears that the therapeutic indices (defined as the ratio of the LD₀ to the minimum dose which produces a significant ILS, that is to say an ILS of 25%) of the two compounds are very greatly above 10. Such high indices are unique in cancer chemotherapy. This means that the anti-tumor activity manifests itself even with a single injection at 1/10 of the LD₀, and that chronic Q1D polyinjection repeated n times, of this very low dose, makes it possible to achieve a cure whilst minimizing the possible secondary effects of the drug.

3. The pharmacokinetics of the action on the tumor, and of the excretion of the medicament, appear particularly advantageous: 9 Q1D injections of 20 mg/kg of SPIRODIAM 3 or SPIRODIAM 4 (in the case of P815) in effect correspond to a total dose, over 9 days, of 180 mg, which is respectively 2.4 and 1.5 times the $LD_0$ of these drugs. In fact, these two protocols do not bring about any cumulative toxicity whatsoever.

The same effect is observed in the case of P388, where 5 Q1D injections of 40 mg/kg, corresponding respectively to 2.7 and 1.6 times the $LD_0$, also do not produce any cumulative toxicity.

4. FIGS. 4 to 9 show the relation ILS= f(dose) for SPIRODIAM 3 and SPIRODIAM 4, used as single injections and Q1D polyinjections, in the case of P388 and P815. The following may be said in connection with these figures:

(a) SPIRODIAM 3 and SPIRODIAM 4 used as a single injection in the case of P388, are characterized by a linear relation ILS=f(dose), (b) SPIRODIAM 3 and SPIRODIAM 4 used as a single injection in the case of P815 are characterized by an ILS=f(dose) relation which has an exponential trend similar to that obtained with SOAz in the case of P388 using DBA/2 female mice, (c) SPIRODIAM 3 and SPIRODIAM 4 used as Q1D polyinjections in the case of P388 and P815 are characterized by substantially linear relations of ILS=f(dose).

5. The following results were observed:

(a) For prostate carcinoma:
9 Q1D injections at 30 mg/kg
T/C (%) SPIRODIAM 3:158% SPIRODIAM 4:154%, (b) In the case of kidney carcinoma:
9 Q1D injections of 20 mg/kg of SPIRODIAM 3
T/C (%): 223%,
9 Q1D injections of 10 mg/kg of SPIRODIAM 4
T/C (%): 155%, (c) In the case of line 26 colon carcinoma:
9 Q1D injections of 10 mg/kg of SPIRODIAM 3
T/C (%): 132%
9 Q1D injections of 20 mg/kg of SPIRODIAM 4
T/C (%): 132%, (d) In the case of Lewis lung carcinoma:
9 Q1D injections of 10 mg/kg of SPIRODIAM 3
TWI %: 43.7.
SPIRODIAM 4 is only active at close to the toxic dose.

In conclusion, SPIRODIAM 3 and SPIRODIAM 4 constitute undoubted improvements over MYKO 63, MYCLAz and SOAz, from the point of view of both the therapeutic index and the anti-tumor activity displayed against tumors in mice.

This latter point is clearly illustrated by Table 2, in which are compared the ILS % obtained with MYKO 63, MYCLAz, SOAz, SPIRODIAM 3 and SPIRODIAM 4 in the case of P388 and P815, using a single injection of, in each case, the same fraction of the $LD_0$.

TABLE 1

| TUMOR | PROTOCOL (intraperitoneal injection) COMPOUND | DOSE (mg/kg/day) | ILS % |
|---|---|---|---|
| P388 | 1 J+1 injection SPIRODIAM 3 | 5 | 30 |
| | | 12.5 | 50 |
| | | 50 | 100 |
| | | 100 | (94)* |
| | 5 Q1D injections | 2.5 | 45 |
| | | 10 | 81 |
| | | 20 | 150 |
| | | 40 | 204 |
| | 1 J+1 injection SPIRODIAM 4 | 12.5 | 50 |
| | | 50 | 74 |
| | | 100 | 103 |
| | 5 Q1D injections | 2.5 | 50 |
| | | 10 | 90 |
| | | 20 | 155 |
| | | 40 | 210 |
| P815 | 1 J+1 injection SPIRODIAM 3 | 12.5 | 55 |
| | | 25 | 70 |
| | | 50 | 150 |
| | | 100 | (95)* |
| | 9 Q1D injections | 1.25 | 50 |
| | | 2.5 | 55 |
| | | 5 | 105 |
| | | 10 | 155 |
| | | 20 | 283 |
| | 1 J+1 injection SPIRODIAM 4 | 12.5 | 45 |
| | | 25 | 65 |
| | | 50 | 90 |
| | | 100 | 535 |
| | 9 Q1D injections | 1.25 | 55 |
| | | 2.5 | 60 |
| | | 5 | 110 |
| | | 10 | 160 |
| | | 20 | 300 |

*toxicity limit

TABLE 2

| TUMOR | PROTOCOL | FRACTION OF THE $LD_0$ | ILS % | | | | |
|---|---|---|---|---|---|---|---|
| | | | MYKO 63 $LD_0$: 40 mg/kg | MYCLAz $LD_0$: 24 mg/kg | SOAz $LD_0$: 210 mg/kg | SPIRODIAM 3 $LD_0$: 75 mg/kg | SPIRODIAM 4 $LD_0$: 125 mg/kg |
| P388 | single injection on J+1 | 1/15 | NS | NS | NS | 30 | 55 |
| | | 1/5 | NS | NS | NS | 50 | — |
| | | 1/4 | 51 | 30 | 35 | — | 70 |
| | | 1/2.5 | — | — | — | — | — |
| | | 1/2 | 101 | 52 | 73 | — | 150 |
| | | 1/1.5 | — | — | — | 100 | — |
| | | 1/1.3 | — | 58 | 134 | — | — |
| | | 1 | tox. | 68 | 196 | — | — |
| P815 | single injection on J+1 | 1/10 | NS | NS | NS | — | 55 |
| | | 1/6 | NS | NS | NS | 55 | — |
| | | 1/5 | 25 | NS | 36 | — | 65 |
| | | 1/3 | — | NS | — | 70 | — |
| | | 1/2.5 | 49 | 27 | 71 | — | 90 |
| | | 1/1.5 | 57 | 40 | 74 | 150 | — |
| | | 1/1.25 | — | 47 | — | — | 535 |
| | | 1 | tox. | 58 | 79 | — | — |
| Type of mouse | | | DBA/2 females | CD2F1 males | DBA/2 females | CD2F1 females | |
| Therapeutic index | P388 | | 5 | 4 | 4 | ~15 | ~15 |

TABLE 2-continued

| TUMOR PROTOCOL | FRACTION OF THE LD$_0$ | ILS % | | | | |
|---|---|---|---|---|---|---|
| | | MYKO 63 LD$_0$: 40 mg/kg | MYCLAz LD$_0$: 24 mg/kg | SOAz LD$_0$: 210 mg/kg | SPIRODIAM 3 LD$_0$: 75 mg/kg | SPIRODIAM 4 LD$_0$: 125 mg/kg |
| P815 | | <5 | 2.5 | 5 | >6 | ~10 |

NS = no significant activity (ILS < 25%)
tox. = toxic

We claim:

1. A compound of the formula I:

in which

Az is 1-aziridinyl,

A is a straight or branched chain alkylene, alkenylene or alkynylene having 1 to 5 carbon atoms, which may be substituted by halo, imino, and amino, and which may be interrupted by —S— or —O—, and $R_1$ and $R_2$, independently of each other, are hydrogen, straight or branched chain alkyl having 1 to 7 carbon atoms, alkenyl having 2 to 7 carbon atoms or alkynyl groups having 2 to 7 atoms, wherein said alkyl, alkenyl and alkynyl groups may be substituted by halo, imino or amino.

2. A compound of the formula I:

in which:

Az is 1-aziridinyl, n is an integer from 1 to 5, $R_1$ and $R_2$, independently of each other, are hydrogen, straight or branched chain alkyl having 1 to 7 carbon atoms, alkenyl having 2 to 7 carbon atoms or alkynyl groups having 2 to 7 carbon atoms, wherein said alkyl, alkenyl and alkynyl groups may be substituted by halo, imino or amino.

3. A compound according to claim 2 wherein n is 2, 3, 4 or 5.

4. A compound according to claim 3 wherein n is 3.

5. A compound according to claim 3 wherein n is 4.

6. A compound according to claim 3 wherein n is 5.

7. A cancer chemotheraputic composition containing an effective amount of at least one compound according to claim 1 as the active principle.

8. A composition according to claim 7, characterised in that it is an injectable composition.

9. A composition according to claim 8, characterised in that it is a composition which may be injected intraperitoneally or intravenously.

* * * * *